United States Patent [19]
Cribbs

[11] 4,265,121
[45] May 5, 1981

[54] HIGH RESOLUTION ULTRASOUND DIAGNOSTIC APPARATUS

[75] Inventor: Robert W. Cribbs, Placerville, Calif.

[73] Assignee: Litton Industrial Products, Inc., Beverly Hills, Calif.

[21] Appl. No.: 959,565

[22] Filed: Nov. 13, 1978

[51] Int. Cl.³ .............................................. G01N 29/04
[52] U.S. Cl. ........................................ 73/607; 73/633
[58] Field of Search ................ 73/606, 607, 620, 633, 73/635, 637, 639; 315/378; 340/5 MP; 128/660

[56] References Cited

U.S. PATENT DOCUMENTS

| | | | |
|---|---|---|---|
| 2,799,157 | 7/1957 | Pohlman | 73/635 |
| 3,006,994 | 10/1961 | Spiegel | 315/378 |
| 3,678,737 | 7/1972 | Miller | 73/639 |
| 3,698,051 | 10/1972 | Miller | 73/639 |
| 3,751,712 | 8/1973 | Murray | 315/378 |
| 3,864,660 | 2/1975 | Ranalli et al. | 128/660 |
| 3,974,826 | 8/1976 | Eggleton et al. | 315/378 |
| 3,980,926 | 9/1976 | Krueger | 315/378 |
| 4,005,258 | 1/1977 | Dory | 73/607 |
| 4,086,818 | 5/1978 | Reynolds | 73/620 |

*Primary Examiner*—Anthony V. Ciarlante
*Attorney, Agent, or Firm*—Robert A. Seldon

[57] ABSTRACT

A high resolution, ultrasound imaging system is disclosed having a transducer which produces a diverging beam of ultrasound energy of sufficiently large angle so as to impinge on the sound-reflecting object from substantially all positions along the transducer scan path.

7 Claims, 10 Drawing Figures

——— WRITE
- - - - - ERASE

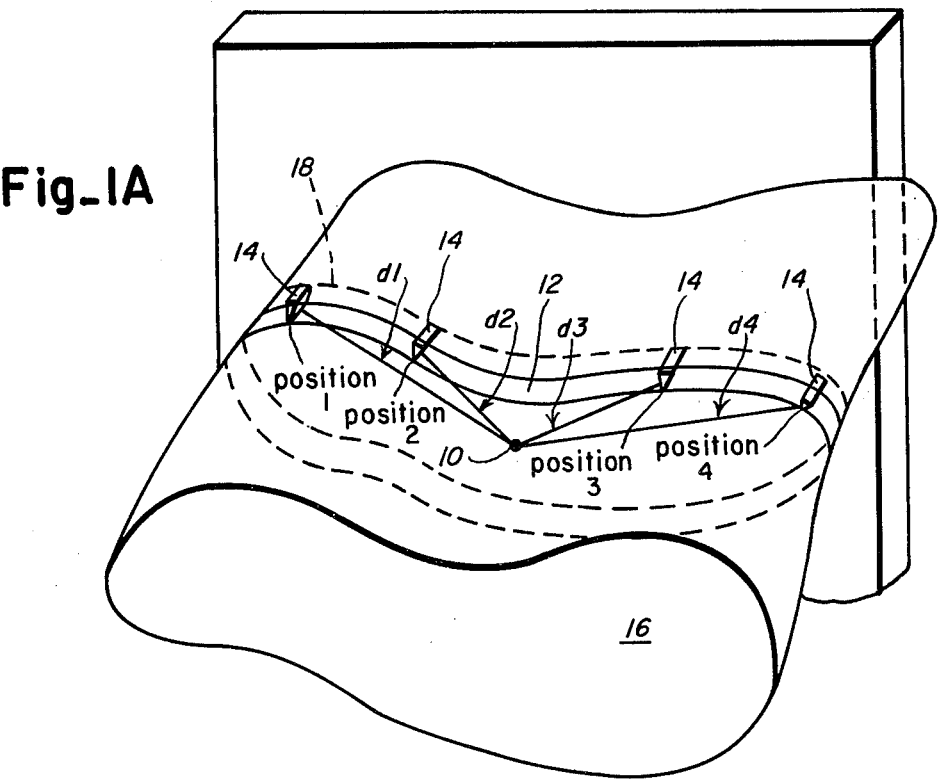
Fig_1A
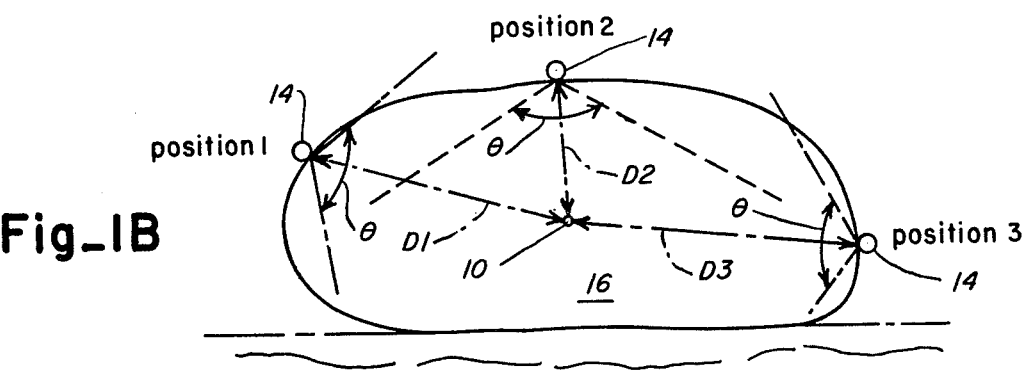
Fig_1B
Fig_6
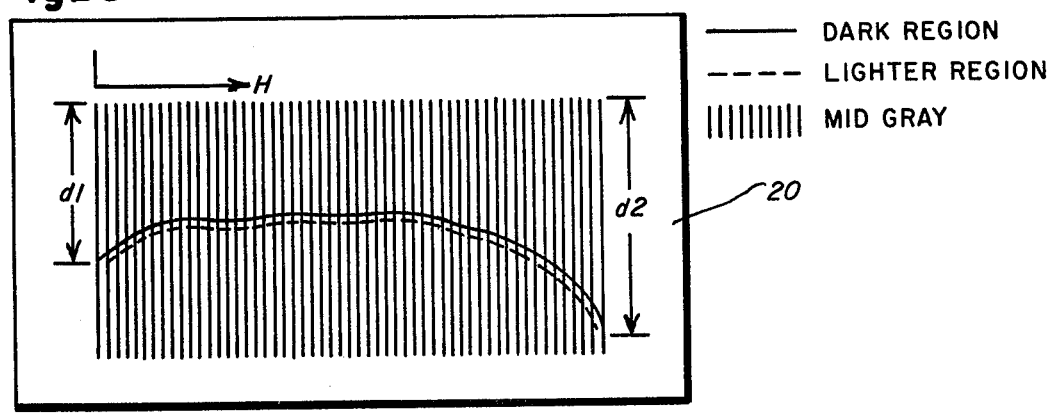
——— DARK REGION
- - - LIGHTER REGION
||||||| MID GRAY

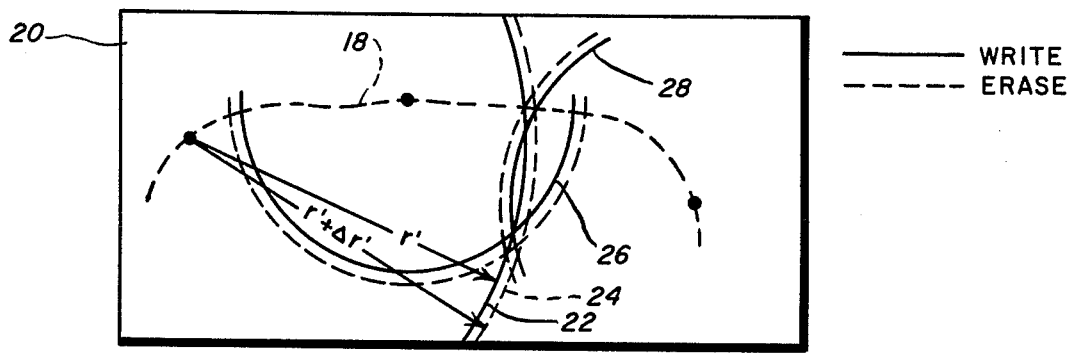
Fig_2
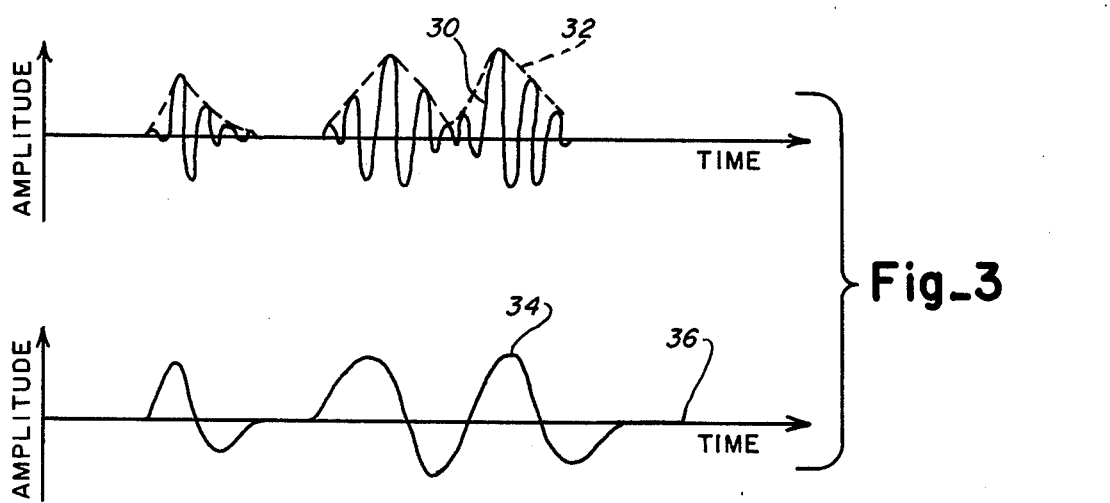
Fig_3
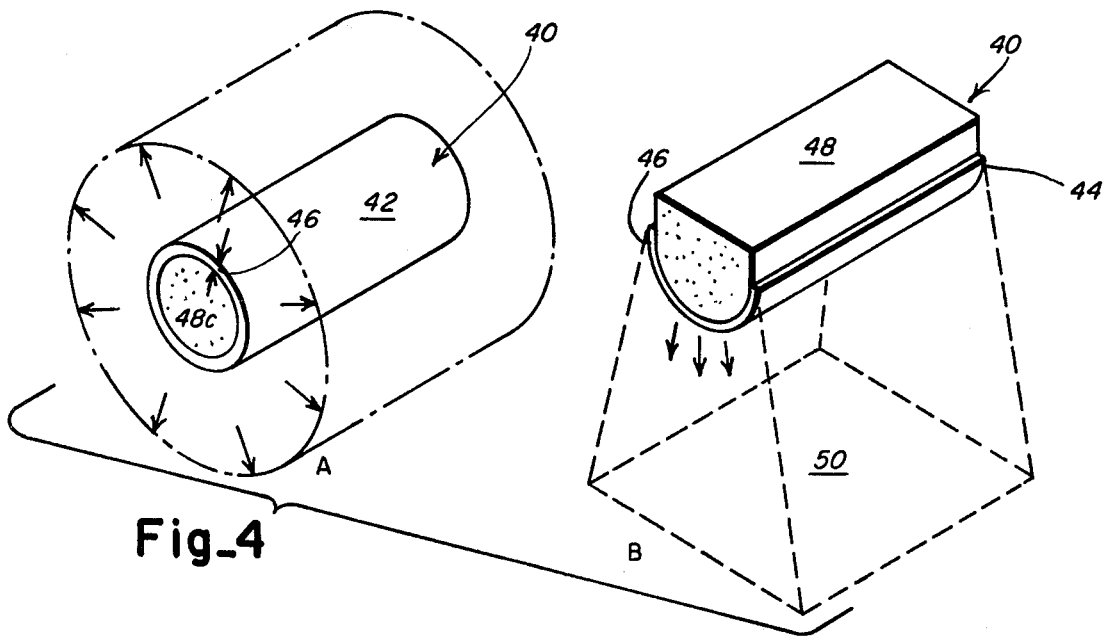
Fig_4

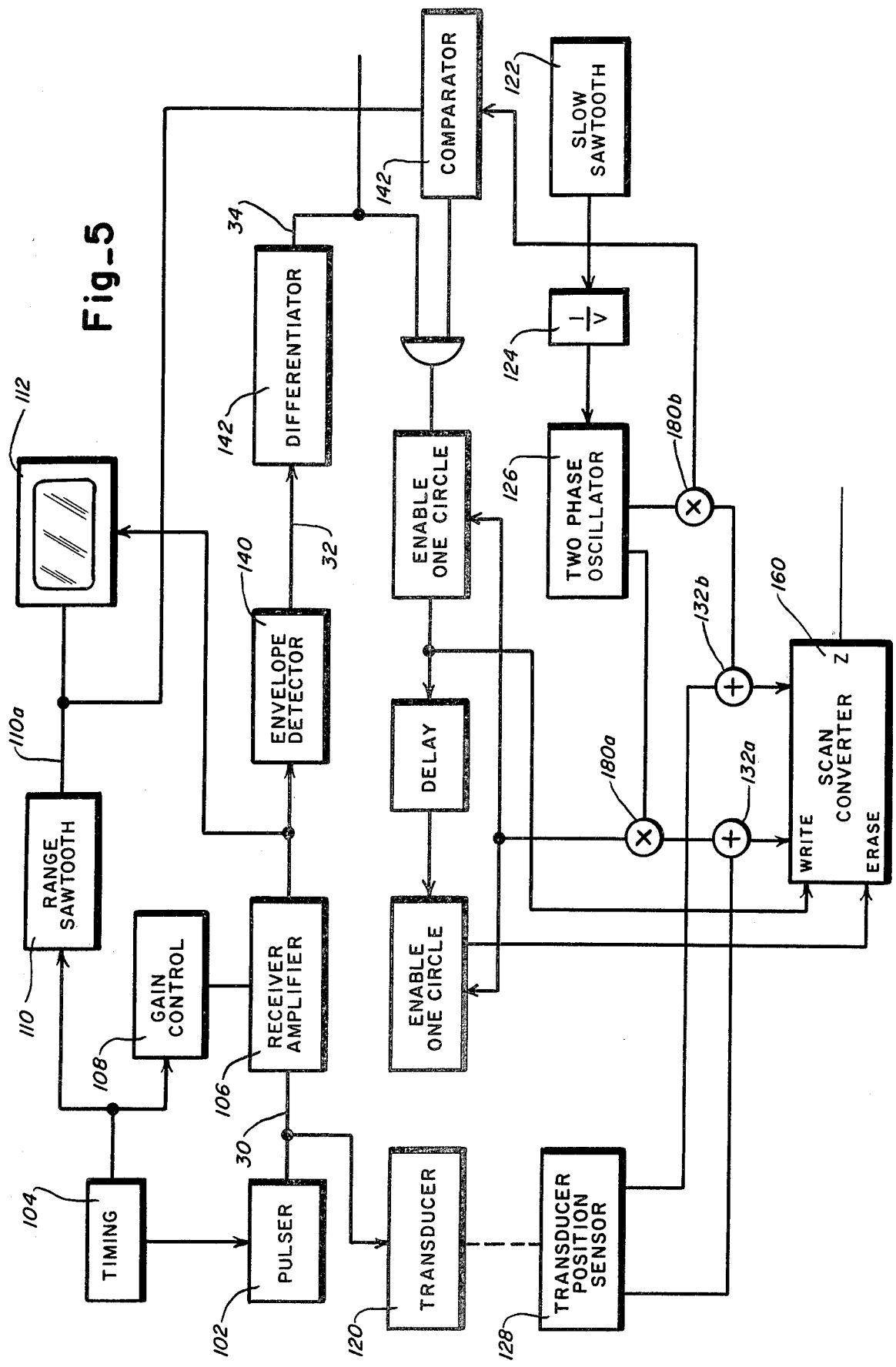
Fig._5

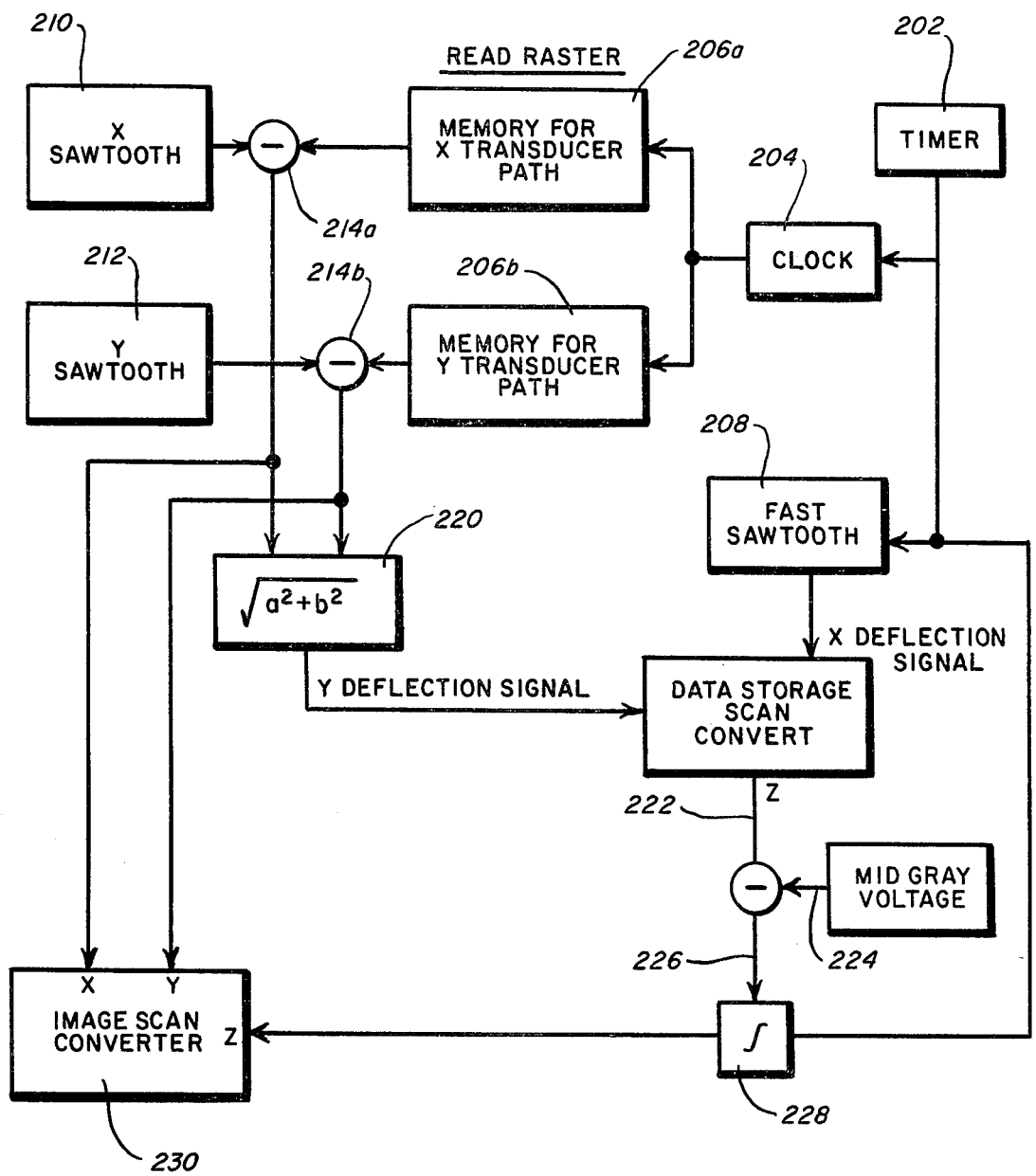

HIGH RESOLUTION ULTRASOUND DIAGNOSTIC APPARATUS

FIELD OF THE INVENTION

This invention relates to imaging systems, such as ultrasound imaging systems, and particularly to imaging systems for producing high resolution images.

Ultrasound systems of the type described herein produce a B-scan image. A B-scan image is an image of an object in a plane through the object where the two dimensions of the B-scan image are the scaled dimensions of the object in the plane, and the gray level of the B-scan image is related to the intensity of the reflected ultrasound intensity at the corresponding location. A transducer is utilized to convert an electrical signal into an ultrasound signal. This signal propagates into the object to be imaged. Irregularities and discontinuities in the object cause ultrasound to be reflected back to the transducers which convert the ultrasound back into electrical signals. These signals are processed to form the B-scan image.

In conventional B-scan imaging a narrow beam is directed into the object to be imaged. The transducer is mechanically constrained to keep the center of the beam in a plane. The signal is generally a short pulse although any signal with wide bandwidth can be used. A straight line raster is created on the imaging surface. It starts at the scaled position of the transducer at the same time as the transducer is pulsed. The raster proceeds in the scaled direction of the beam at a rate corresponding to one-half the scaled velocity of sound in the object being imaged. The echos that are received by the transducer are used to intensify the raster and make a permanent mark on the B-scan image.

It is well-known that the range resolution of ultrasound or radar is determined by the bandwidth of the signal, and the lateral resolution is determined by the size of the aperture of the transmitting and receiving antennas or transducers. Two objects at the same lateral position can be resolved if they differ in range by $\Delta R$ where $$\Delta R = V/2B \quad (1)$$

where
V = velocity of propagation
B = bandwidth of the signal

Two objects at the same range can be resolved if they are laterally separated by S where $$S = 1.22 \, VX/Af \quad (2)$$

where
X = distance from transducer to objects
f = frequency of signal
A = aperture or diameter of transducer or antenna
V = velocity of propagation S cannot be smaller than $\Delta R$ so if Equation 2 yields S smaller than $\Delta R$ the lateral resolution is $\Delta R$; that is the lateral and range resolution are the same.

SUMMARY OF THE INVENTION

The novel imaging system described herein utilizes an ultrasonic beam that illuminates substantially the entire image plane. The path of the transducer is arbitrary; it may move along a complex surface of the subject to be imaged. The transmitted signal can be a short pulse or any other wideband signal.

In the first method of signal processing, a circular raster is generated that starts at the scaled position of a generally cylindrical transducer at the same time the pulse is transmitted. As the pulse expands radially, the circular raster expands at a rate equal to one-half the scaled velocity of sound. If a short pulse is used, the echos received are envelope detected. The envelope is differentiated. The writing surface is prepared by starting at mid gray. If the derivative is positive, the raster beam writes a circular arc. If negative, the raster erases a circular arc. This process forms the image.

In many practical instances, the raster cannot be created fast enough because of the finite bandwidth of the deflection circuits associated with the system display. In this case the return echos must be memorized in either an analog or digital memory register and clocked into the write/erase electronics at a rate commensurate with the maximum rate that the raster can be generated.

Accordingly, in a second method of signal processing, the same transducer, beam shape, and pulse shape are used. The imaging is formed in two steps rather than one. In the first step, the differentiated envelope is recorded in memory.

If the memory is a scan converter, the horizontal raster position is proportional to the number of pulses transmitted from the beginning of the scan. The vertical raster starts at the same time the pulse is transmitted and slews vertically; generally at a constant rate.

At each pulse, the horizontal and vertical coordinate of the center of the transducer are converted to digital coordinates and memorized in a digital memory.

A raster is created to read the data in the following way:

Th gray level of the image at Cartesian coordinates (x,y) in the scaled image plane is determined by integrating the output of the read raster that scans across the data. The read raster travels horizontally across the data at a constant rate. The vertical position of the read raster at a position corresponding to the $n^{th}$ pulse after the start of data collection is $$V_n = \sqrt{(x - x_n)^2 + (y - y_n)^2} \quad (3)$$

where $x_n$ and $y_n$ are the (x,y) coordinates of the transducer at the $n^{th}$ pulse.

The x and y coordinates of the image are varied in TV format. The integrated signal modulates the intensity of the image surface to form the image.

Further details are set forth below in a detailed description of the preferred embodiment which is to be read in conjunction with the drawing.

BRIEF DESCRIPTION OF THE DRAWING

In the drawing,

FIG. 1A is an isometric illustration of an examined body,

FIG. 1B is an elevation view of the image plane in FIG. 1A

FIG. 2 is a diagramatic representation of data written on a storage surface in accordance with the invention FIG. 3 is a graphic illustration of the electrical waveforms representing incoming pulse-reflection data FIGS. 4A and 4B are isometric views of alternative onstructions for transducers which may be used in the ᴄ scribed imaging system FIG. 5 is a block diagram representation of an imaging system constructed according to the teaching herein FIG. 6 illustrates an alternative format for writing data on a storage surface FIG. 8 is a block diagram showing the circuitry for reading the data from the storage surface of FIG. 6 for display.

DETAILED DESCRIPTION OF THE PREFERRED EMBODIMENT

Figure 7:
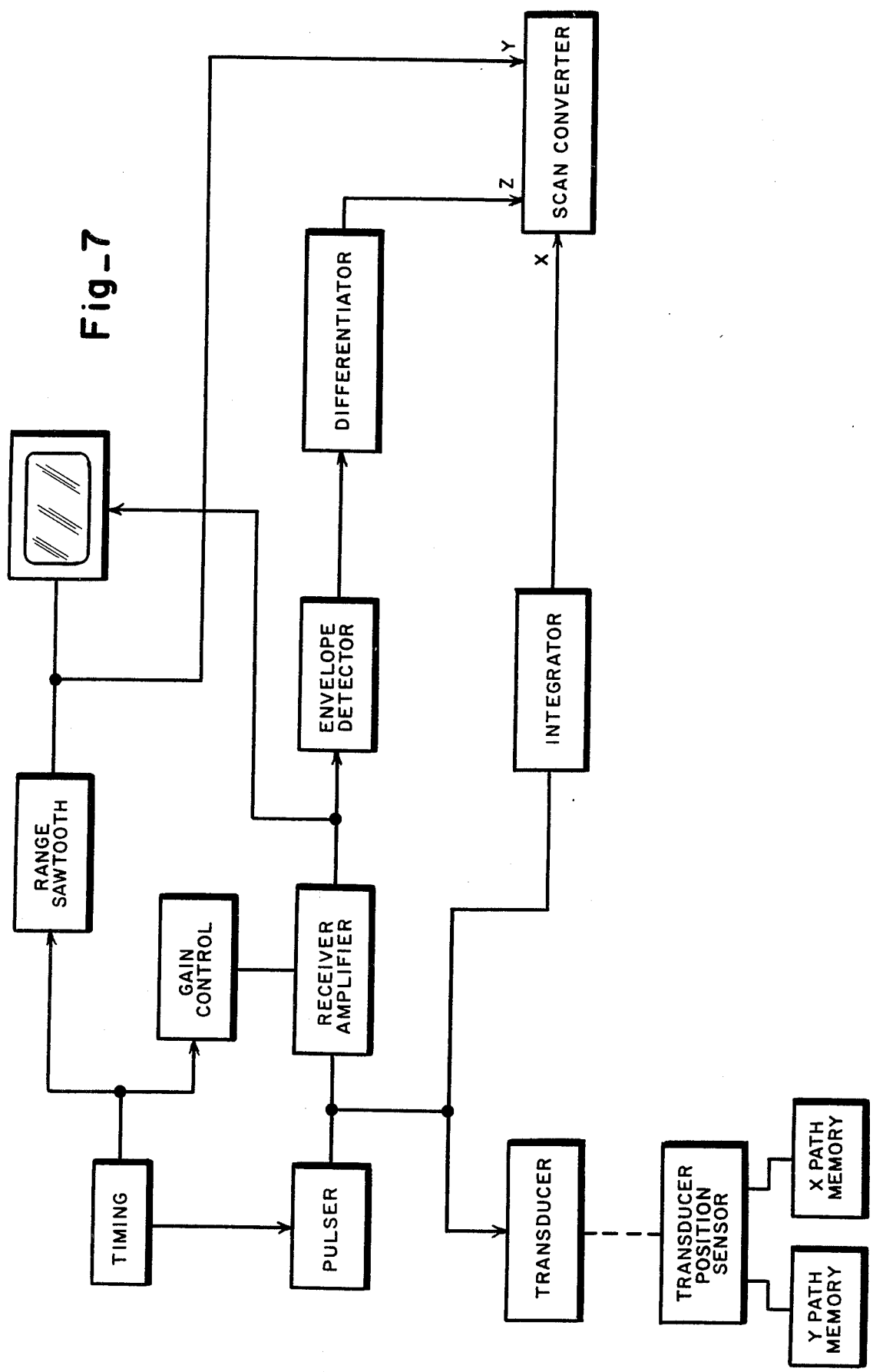
FIG. 7 is a block diagram representation showing a system for reading data on the storage surface of FIG. 6.

Turning initially to the one-step signal-processing technique referenced above, attention to direct to FIGS. 1A and 1B which illustratively depict the scanning of an object 16 containing a target 10 in plane 12. A transducer 14 is scanned along the surface of an object 16 from position 1 to position 4 along a surface path 18. As the transducer 14 travels it emits pulses of ultrasound. The transducer is designed to send an expanding circular wave in the plane with the transducer at the center. At position 1, for example, an echo from the reflector 10 arrives back at the transducer at time $$T = 2d_1/V \qquad (4)$$

where
$d_1$ = distance from the transducer to the reflector
$V$ = velocity of sound propagation On the basis of the return echo from position 1, there is only enough information to establish that the relfector is somewhere on a circle of radius $d_1$, centered at position 1 having Cartisian coordinates $(x_1, y_1)$.

A storage surface 20, depicted in FIG. 2, is prepared for imaging by writing the surface to mid gray. The image is started by writing, on the surface 20, a circular arc 22 radius r' and center (x',y') where $r' = cd_1$, $x' = cx_1$, $y' = cy_1$, etc., where C is the scaling constant required to have the image substantially fill the storage surface and $d_1$, $x_1$, and $y_1$ are the parameters illustrated in FIG. 1. The writing beam is set to produce only a few percent increase in gray level above the 50% level already there. A second arc 24 with the same center but larger radius, $r' + \Delta r'$, is erased. The beam is adjusted to erase the same percentage gray level as the first circle writes. The difference in circle size, $\Delta r'$, is somewhat arbitrary, but best results are achieved if $\Delta r'$ is chosen to be the system resolution, about one wavelength for most modern ultrasound systems.

The write/erase intensity level is determined from the amplitude of the return echos. Turning to FIG. 3, a typical return echo is shown. An envelope 32 of the signal is formed and differentiated, the differentiation being graphically depicted at 34. The write level of the arc 22 (FIG. 2) is related to the distance above the zero line 36 (FIG. 3) of the curve 34; the erase level for the arc is similarly proportional to the distance below the line 36 of the curve 34.

A transducer 40 constructed in accordance with the present invention is shown in FIG. 4 as made from a piezoelectric cylinder 42 or a section 44 of the cylinder. The cylinder is long enough to keep the ultrasound signal from expanding from the image plane in the region of interest. The length of the cylinder to do this is approximately $$L = R\lambda \qquad (5)$$

where
$R$ = the distance from the transducer to the point where the beam must be columinated
$\lambda$ = the wavelength of sound The thickness 46 of the transducer is about ½ wavelength of the sound pulse. The center of the transducer is filled with a sound absorbing material 48.

The transducer may be the cylinder 42 if the transducer is scanned through a liquid and imaging of the region on both sides of the path are required. The section 44 of the cylinder may be used if the object to be imaged lies on one side of the scan path.

FIG. 2 illustrates the arcs associated with three typical pulses. Each echo is processed as described in detail below with write arcs 26, 28 centered at the respective scaled transducer focal spot positions 2 and 3 (FIG. 1B) and having a radius equal to the scaled distance between the transducer focal spot and reflector. Erase arcs 26', 28' are formed in a manner similar to arc 24. At the scaled position of the target 10 on the storagesurface 20, all the write circles intersect. This creates a white dot. A black region may occur around the dot due to the buildup of erase marks. On all other parts of the screen, there is one erase and one write which cancel each other, leaving mid gray. There will be one erase circle at the start of the scan and one write circle at the end that is not cancelled, but this will be barely visible when viewing the surface because it is only a few percent of the total gray scale. The image is conveniently viewed by adjusting the reading beam so that mid gray is black and white is white. Thus, only the portion of the image above mid gray is viewed.

The image that results is a white dot at a scaled position corresponding to the target. If there were several targets, each would be imaged at their corresponding positions. Furthermore, if there were an extended target in the image plane rather than a point target, it would be similarly imaged; an extended target is imaged because the tangent of the write circle "rolls" along the target and is not cancelled by the erase circle. Thus, a cross-sectional image is produced.

Having described the one-step method above, attention is directed to FIG. 5 and a preferred analog system configuration, although it will be understood that digital components and techniques may be used to provide an equivalent system.

The surface on which the image is formed is basic to the invention. A scan converter may be used and may be either single-ended (one beam for write, erase, and read) or double-ended (write and erase beam on one side of the storage surface and read beam on the other). A storage oscilloscope tube with selective erase capabilities can be used with no read beam required, but at the present state of the art, they lack resolution and dynamic range of gray scale for high quality images. Naturally, a digital scan converter may be employed in accordance with knowledge and techniques known in the art.

In this scan converter system, the writing surface is displayed on a television monitor by giving the sytem a "television read" command.

The writing surface is prepared by taking it to mid gray. A TV write command is given with the video input voltage set to write the screen to mid gray. The writing is in a standard TV raster format. To avoid having raster lines appear, the write beam is de-focused.

A transducer 120 required for this invention produces a generally cylindrical beam and can be built from a section of a cylindrical piezoelectric as described above. The transducer can have internal focus or external focus. The external focus is preferred when the transducer is in one media, for example water, and the object to be imaged is another, such as steel. If this is the case, the preferred position of the focal spot is the interface between the two media.

In this embodiment the transducer 120 has a thickness corresponding to a resonance of 2 MHz, a radius of 0.5 inch and a length of 1 inch. As shown in FIG. 4, the beam 50 produced by this transducer lies primarily between two planes perpendicular to the axis of the piezoelectric through its center, although in fact, the beam has a finite width perpendicular to the plane. The axial length of the transducer is chosen by rules given above.

The image forming system, shown in FIG. 5, includes components which are found in many commerical ultrasound systems: a pulser 102, a timing means 104, a receiver amplifier 106, gain control 108, a sawtooth generator 110, and oscilloscope A display 112.

The image-forming system additionally includes a raster generator which provides the x and y deflection signals during the image formation process. The raster generator consists of a slow sawtooth voltage generator 122, a reciprocal generator 124, a two-phase voltage controlled oscillator 126, a transducer position sensor 128, a multiplier circuit 180, and an adder circuit 132.

The transducer position mechanism 128 must give two voltages proportional to the Cartisian coordinates of the focal point of the transducer. In the simplest case, the transducer is moved along a lead screw. The y coordinate is chosen to be the vertical position of the transducer. In this example, the y coordinate does not change. There is a requirement that the number of pulses per unit travel of the transducer be approximately constant. This can be accomplished by pulsing at a constant rate and traversing the transducer at a constant rate.

In the preferred embodiment, the voltages chosen to position the writing and erase beam are $-0.5$ to $+0.5$ v for left to right and $-0.4$ to $+0.4$ v for bottom to top deflection of the video beam. This writes on an area with a 4×5 aspect ratio. The position mechanism the produces a $+0.4$ volt to $-0.4$ volt signal as the lead screw moves the transducer from left to right. The y coordinate is a constant chosen to be $+0.3$ volts because all the targets are below the scan line.

The slow sawtooth generator 122 generates a ramp voltage that represents the range from the center of the transducer to the point to be imaged.

The two-phase oscillator 126 generates two sine waves 90° out of phase. These voltages create a circular raster when applied to the x and y deflection circuits. The frequency of the circle must be high for small diameter circles and low for large circles to achieve a constant slew rate on the writing surface. This is accomplished by generating a voltage proportional to 1/v (where v is the vertical distance of the propogating pulse from the transducer focal spot) and using this to control the frequency of the two-phase oscillator 126. The output of the oscillator is multiplied at 180 by the ramp voltage from the slow sawtooth generator 122 to create a circular raster whose diameter is proportional to the ramp voltage.

Voltage from the sensor 128, proportional to the x and y transducer positions, are then added to the sine waves from the oscillator 126. The signal created consists of expanding circles centered at a position scaled to the x-y position of the transducer. These signals provide the x and y deflection signals during the image formation process.

Turning to the processing of the received reflections from the examined body, the received signal 30 is passed through an envelope detector 140 and differentiator 142 to produce the signals shown in FIG. 3.

The intensity (z) axis of the system scan converter 160 is actuated by an echo received. The returning echos are converted by the receiver 106 to an electrical signal 30 representatively illustrated in FIG. 3. The signal 30 passes through an envelope detector 140 and differentiator 142 to yield signals 32, 34 (FIG. 3) respectively. The signal 34 initiates a write command for one circle. After a delay period, an erase circle is initiated. Attenuators in the write and erase lines balance the signals so that the write and erase produce equal effects.

The pulser timing 104 is not critical. It is sufficient that the repetition rate be low enough that range ambiguities do not occur. For this example 1000 pulse-per-second was used.

The pulse actuates the fast sawtooth generator 110. This sawtooth voltage 110a is compared with the output from the slow sawtooth generator 122. When they are the same, a write/erase sequence is recorded. Because the echo is sampled at only one range during each transmission, several hundred pulses must be transmitted at each transducer location.

Many improvements in the foregoing embodiments are within the scope of the present invention. For example, a faster imaging operation could be achieved by storing the received echoes in a memory. Then the slow saw and fast sawtooth would have the same repetition rate. The speed of the slow sawtooth would be limited by the slew rate limitation of the scan converter. For example, with a frequency limitation of 500 KHz and 500 range resolution elements and pulses at 500 transducer locations, each raster would take 6 seconds rather than 6×500=3000 seconds.

Returning to the earlier reference to a two-step process, the transducer, beam shape, signal, and scan path are the same as in the one-step processing. The raster for recording the ultrasound data does not produce an image, but provides an intermediate storage area. The data is read by a read raster beam, processed, then placed on a second scan converter as an image. The advantage of the two-step processing is that the ultrasound data can be recorded in a simple format for fast data collection.

In the first step, the data is written on the recording surface 20 in the format shown in FIG. 6. The horizontal raster position H is proportional to the number of pulses transmitted from the beginning of data collection. A vertical sawtooth starts when the pulse is transmitted and proceeds vertically at a rate proportional to the velocity of sound. Approximately 1000 pulses are transmitted to create an image. The circuit block diagram for recording data is shown in FIG. 7.

No surface preparation is required as in the previous version. With no echoes, the derivative is constant, and this constant level is chosen to be mid gray. When the derivative is positive, the signal writes above mid gray;

when the derivative is negative, the signal writes below mid gray.

The plane in which the transducer is scanned is described by Cartesian coordinates x and y. The position of the focus of the transducer at the $n^{th}$ pulse is $x_n$ and $y_n$. These coordinates are memorized and placed in a memory as the scan proceeds. The $n^{th}$ memory location contains the coordinates $x_n$ and $y_n$.

When the data is to be read from memory, a read raster is used which scans the data horizontally at a constant rate. If the picture element (pixel) at image location x and y is being generated the vertical position of the read raster beam at the $i^{th}$ echo position is $$y_i = (x - x_i)^2 + (y - y_i)^2 \qquad (6)$$

where x and y are the coordinates of the transducer focus during the $i^{th}$ pulse.

The read raster is generated by the circuit in FIG. 8. A timer circuit 202 creates a pulse for each pixel. The pulse actuates a clock 204 that clocks the x and y locations of the transducer path from memory 206 a, b respectively. At the same time a sawtooth is generated by means 208 that deflects the beam horizontally. The sawtooth is synchronized so that when it produces a voltage corresponding to the $i^{th}$ storage pulse, $x_i$ and $y_i$ come out of memory.

The location of the pixel to be imaged is generated with the x and y sawtooth generators 210, 212 respectively. If the dimension of the image is N by M pixels, the x sawtooth generator 210 generates one sawtooth each time the fast sawtooth generator 208 generates N sawtooths, and the y sawtooth generator 212 generates M sawtooth. When the y sawtooth generator completes one sawtooth, the image is complete.

The x and y location of the pixel is substrated from the x and y location of the transducer by means 214. These signals enter a circuit 220 for taking the square-root-of-the-sum-of-the-squares of the inputs. This signal appropriately scaled, produces the y deflection.

The intensity output 222 of the scan converter is subtracted from a voltage 224 corresponding to the mid gray level and the resulting signal 226 is integrated by means 228 for the period of time of the fast sawtooth from generator 208. The final value of this integral is used to intensity modulate the intensity axis of the scan converter 230 containing the image.

While the foregoing description is of a preferred embodiment of the invention, it is recognized that many variations and modifications may be made without departing from the spirit and scope of the invention. Accordingly, the appended claims should be given the broadest scope possible in view of the prior art so as to encompass those changes which are obvious to those skilled in the art.

I claim:

1. An imaging system for examining an area comprising:
    transducer means for generating and transmitting pulses of wide frequency bandwidth energy into the examined area and for receiving echos reflected from an object in said area, said transducer means further having means for developing a first set of signals in response to return time and magnitude of the echos;
    means for translating said transducer means along a scanning path in the vicinity of the examined area and for developing and recording a second set of signals in response to the position of said transducer means along the scanning path;
    means on said transducer means for producing a beam of energy having an angle sufficiently large to impinge on said object from substantially all positions of the transducer means on the scanning path;
    means for displaying multi grey level images on a display surface, the images having length and width dimensions corresponding to length and width dimensions of object in the examining area and including a storage surface;
    means for processing said first and said second set of signals and applying said processed signals to said displaying means.

2. The system of claim 1 wherein said system further comprises
    means for initializing the display means at a generally mid-grey level
    means for generating a circular raster generally simultaneously with each transmitted pulse, the radius of the raster being proportional to the elapsed time since pulse transmission into the area,
    write means responsive to the receipt of an echo for writing an echo-related raster on the storage surface, the echo-related raster being centered at an image position in response to the second set of signals and having a radius determined by the echo return time, said write means thereafter erasing a raster of incrementally different radius.

3. The combination of claim 1 wherein said processing means comprises:
    means for detecting an envelope of the first set of signals;
    means for differentiating said envelope;
    means for generating a circular raster simultaneously with each transmitted pulse, each raster being responsive to the second set of signals for determining the center thereof said raster also being responsive to the derivative developed from the detected envelope of the first set of signals to write and erase circles on said display areas, said write circles being responsive to positive derivatives and said erase signals being responsive to negative derivatives.

4. The combination of claim 1 wherein said processing means comprises:
    means for storing said first set of signals;
    means for reading said stored information and processing a third set of signals for applying said third set of signals to said displaying means.

5. The combination of claim 1 wherein said processing means comprises:
    means for detecting an envelope of the first set of signals;
    means for differentiating said envelope;
    means for recording and storing said differentiated envelope on a scan converter;
    means responsive to said recorded and stored information for generating an image on an image scan converter.

6. The combination of claim 1 wherein said displaying means comprises an image scan converter.

7. The combination of claim 4 wherein said means for storing said first set of signals comprises a data storage scan converter.

* * * * *